(12) United States Patent
Figley et al.

(10) Patent No.: US 6,955,171 B1
(45) Date of Patent: Oct. 18, 2005

(54) SYSTEM AND METHOD FOR DELIVERING THERAPEUTIC GAS TO A PATIENT

(75) Inventors: Curtis Figley, Edmonton (CA); Darin W. Hunt, Edmonton (CA); Christopher C. Miller, North Vancouver (CA)

(73) Assignee: Pulmonox Technologies Corporation, Edmonton (CA)

( * ) Notice: Subject to any disclaimer, the term of this patent is extended or adjusted under 35 U.S.C. 154(b) by 337 days.

(21) Appl. No.: 10/140,304

(22) Filed: May 7, 2002

Related U.S. Application Data

(63) Continuation-in-part of application No. 09/688,229, filed on Oct. 16, 2000, now Pat. No. 6,668,828.

(51) Int. Cl.[7] ............................................. A61M 16/00
(52) U.S. Cl. .............................. 128/204.21; 128/204.23
(58) Field of Search ...................... 128/200.24, 204.18, 128/204.21, 204.23, 202.22, 203.12, 203.13, 128/203.14, 203.22, 205.24, 205.23, 205.11, 128/910

(56) References Cited

U.S. PATENT DOCUMENTS

| | | | |
|---|---|---|---|
| 2,915,056 A | 12/1959 | Lee | |
| 4,148,312 A | 4/1979 | Bird | |
| 4,442,856 A | 4/1984 | Betz | |
| 4,462,398 A | 7/1984 | Durkan | |
| 4,702,240 A | 10/1987 | Chaoui | |
| 4,932,401 A | 6/1990 | Perkins | |
| 5,423,313 A | 6/1995 | Olsson | |
| 5,531,218 A | 7/1996 | Krebs | |
| 5,558,083 A * | 9/1996 | Bathe et al. | 128/203.12 |
| 5,592,934 A | 1/1997 | Thwaites | |
| 5,615,669 A | 4/1997 | Olsson | |
| 5,651,358 A | 7/1997 | Briend | |
| 5,692,497 A | 12/1997 | Schnitzer | |
| 5,713,349 A | 2/1998 | Keaney | |
| 5,752,504 A | 5/1998 | Bathe | |
| 5,865,174 A * | 2/1999 | Kloeppel | 128/204.23 |
| 5,873,359 A | 2/1999 | Zapol | |
| 5,918,596 A | 7/1999 | Heinonen | |
| 6,089,229 A * | 7/2000 | Bathe et al. | 128/204.21 |
| 6,109,260 A | 8/2000 | Bathe | |
| 6,142,147 A | 11/2000 | Head | |
| 6,164,276 A | 12/2000 | Bathe | |
| 6,308,703 B1 * | 10/2001 | Alving et al. | 128/203.12 |
| 6,581,599 B1 * | 6/2003 | Stenzler | 128/204.23 |
| 6,668,828 B1 * | 12/2003 | Figley et al. | 128/204.18 |
| 6,786,217 B2 * | 9/2004 | Stenzler | 128/204.23 |

FOREIGN PATENT DOCUMENTS

EP 640357 3/1995

* cited by examiner

Primary Examiner—Teena Mitchell
(74) Attorney, Agent, or Firm—Terry M Gernstein

(57) ABSTRACT

Therapeutic gas, such as NO, is delivered to a patient in accurately controlled amounts by a system that uses a closed loop feedback system in which the amount of therapeutic gas delivered is a precise fraction of the total gas delivered to the patient. Ratiometric feedback is used in the control loop.

20 Claims, 7 Drawing Sheets

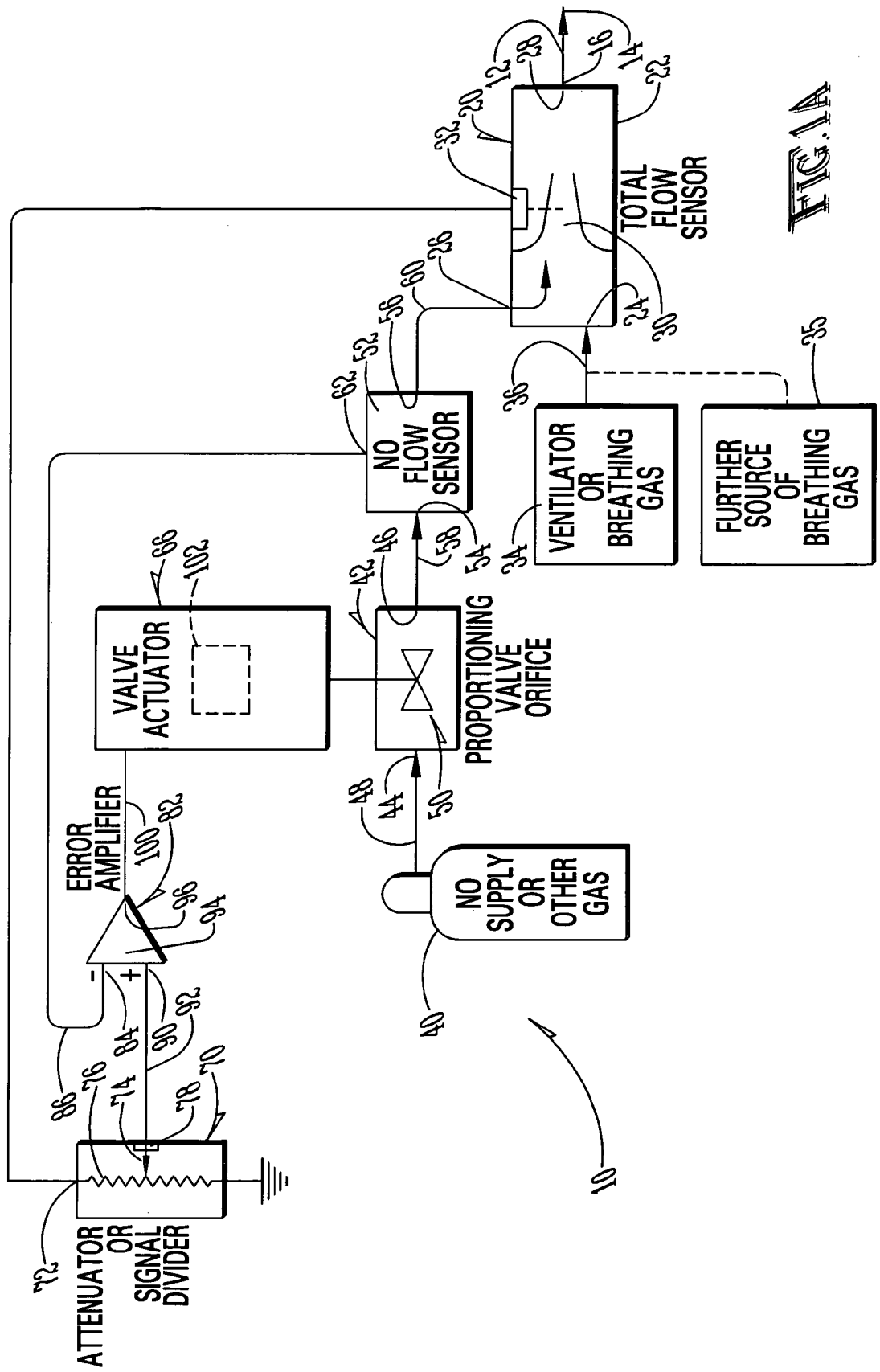

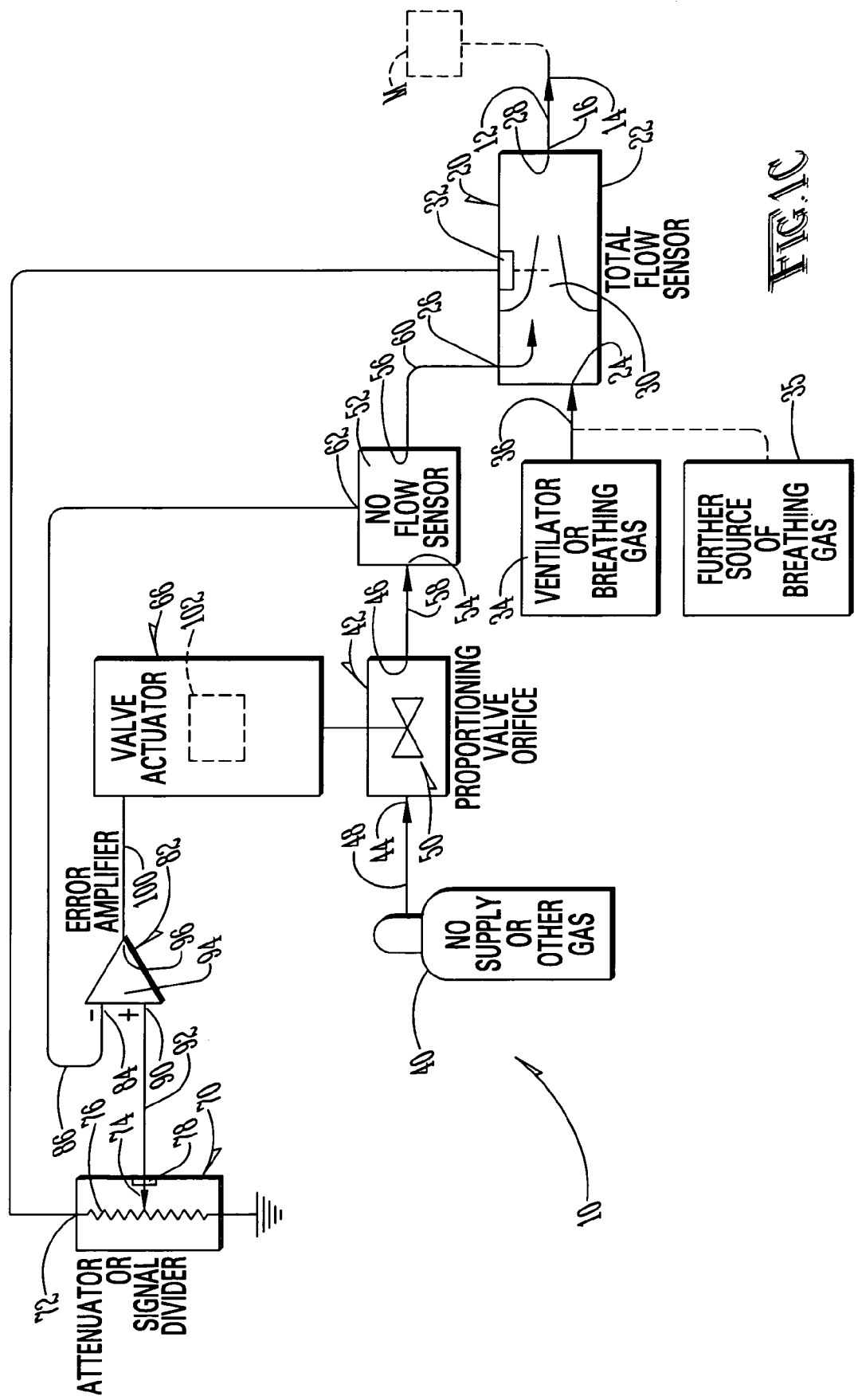

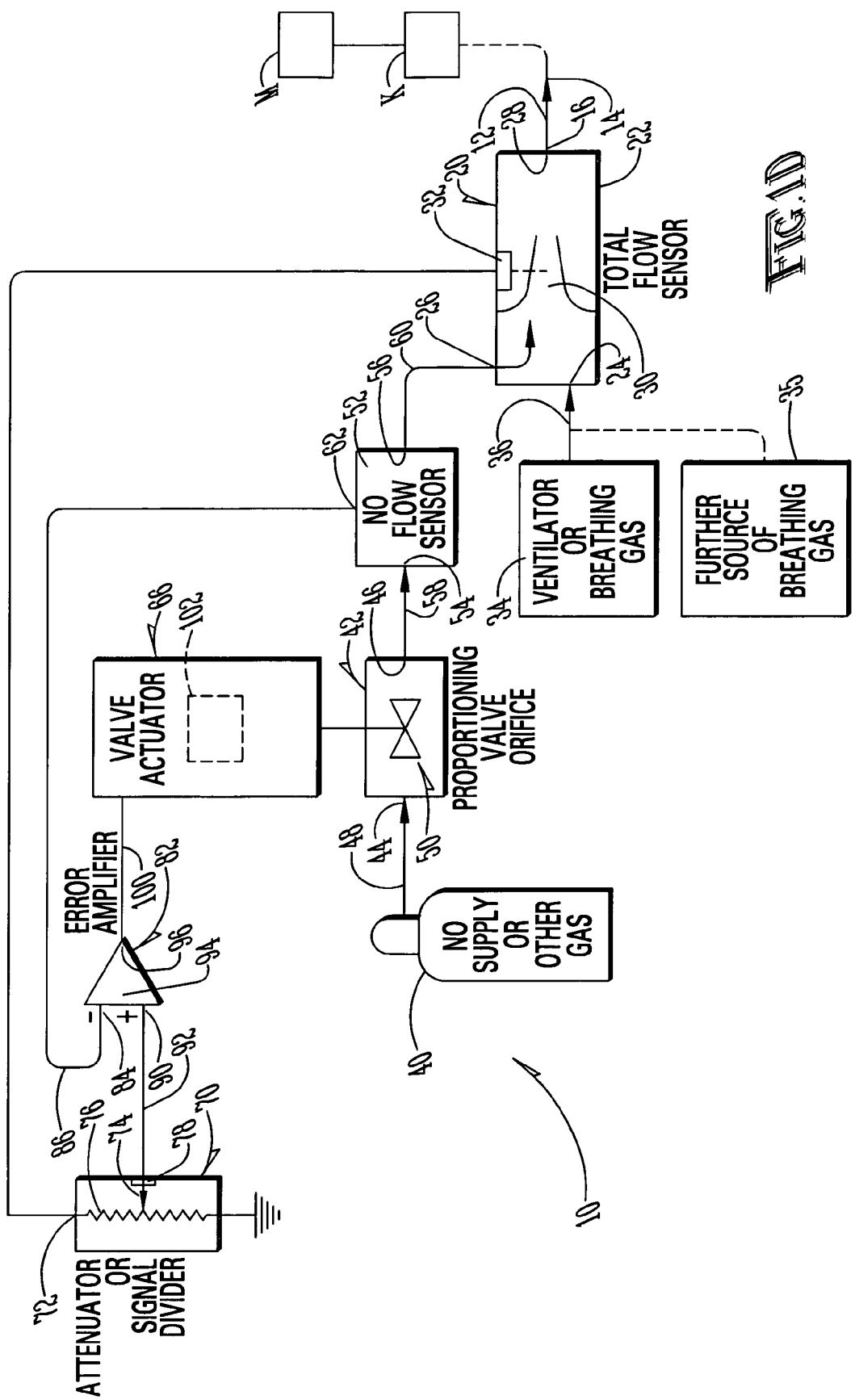

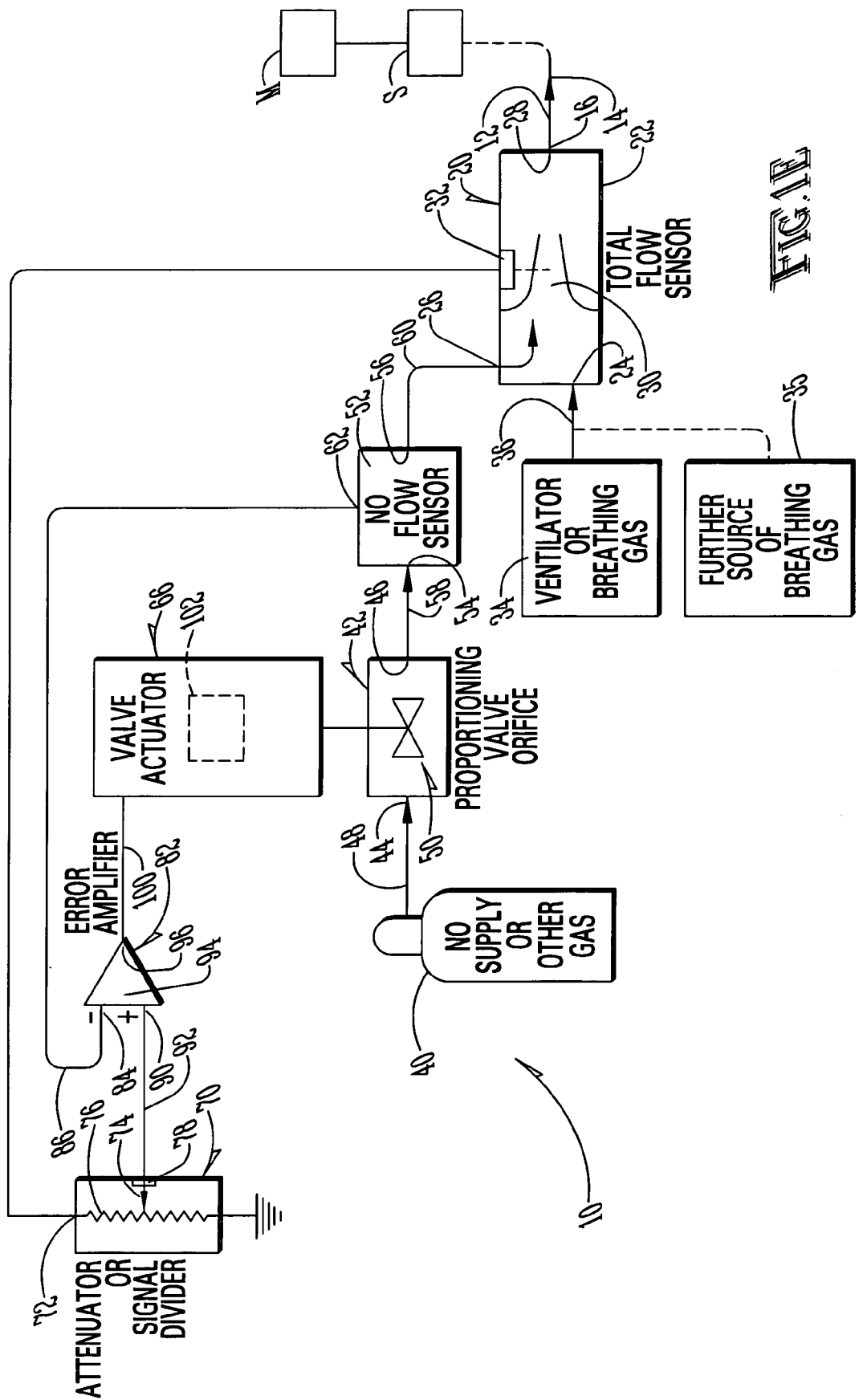

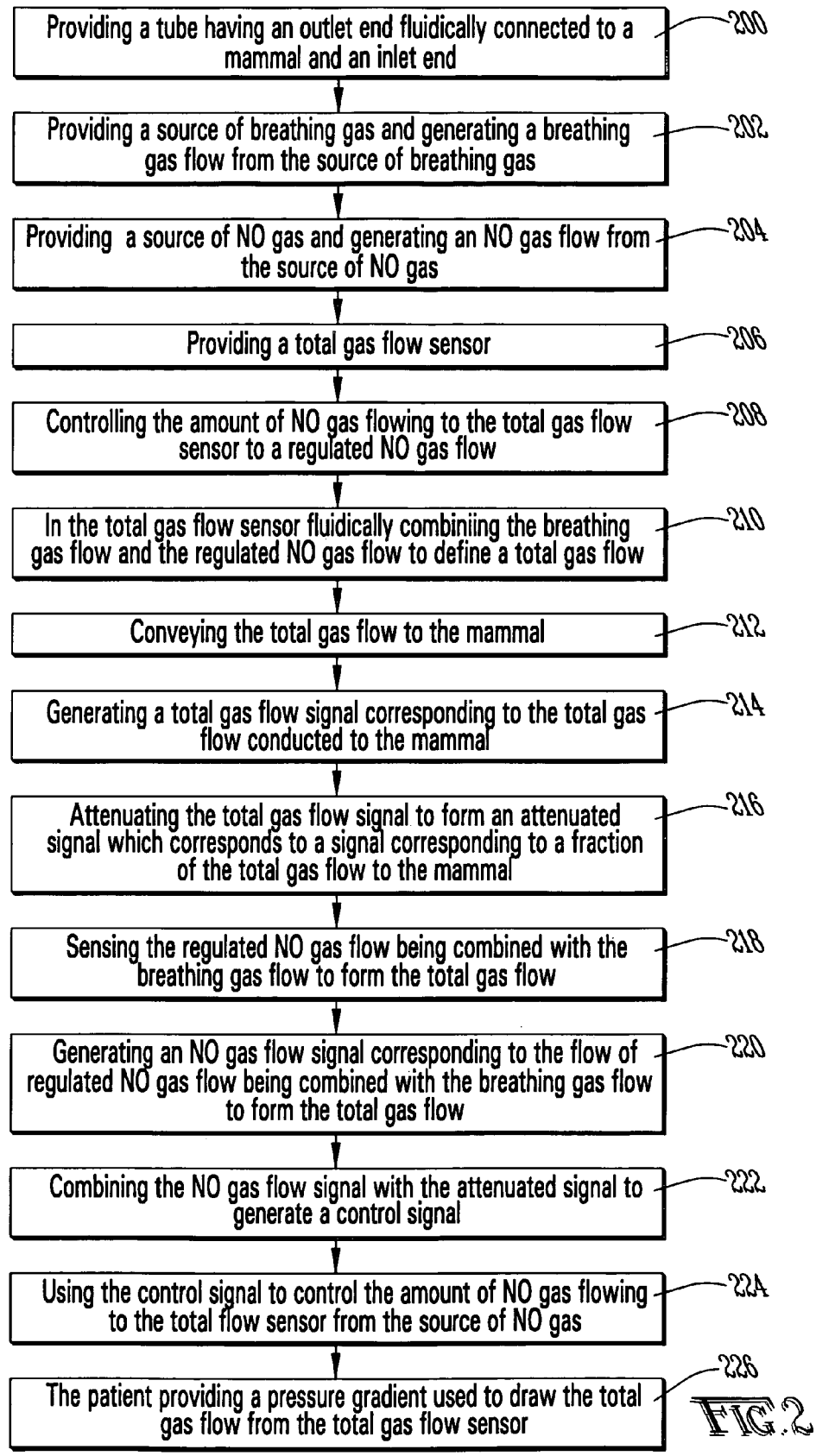

SYSTEM AND METHOD FOR DELIVERING THERAPEUTIC GAS TO A PATIENT

CROSS REFERENCE TO RELATED APPLICATIONS

The present application is a continuation-in-part application of Ser. No. 09/688,229, filed on Oct. 16, 2000 and issued on Dec. 30, 2003 as U.S. Pat. No. 6,668,828 and incorporates by reference the disclosure of such application. The present application incorporates by reference the disclosure of this application and also incorporates by reference the disclosure of applications, U.S. Ser. No. 09/836,603, titled "System and method for the prevention of infections in human patients using nitric oxide" and filed on Apr. 18, 2001, now abandoned, as well as the disclosure of U.S. Ser. No. 09/816,104, titled "System and method for the prevention and treatment of animal wound infections using nitric oxide" and filed on Mar. 26, 2001, now abandoned.

TECHNICAL FIELD OF THE INVENTION

The present invention relates to the general art of surgery, and to the particular field of mixing treating agents and speciality medical gases with respiratory gas.

BACKGROUND OF THE INVENTION

As discussed in the incorporated documents, the use of nitric oxide (NO) to treat mammals has been known in the art for some time. The administration of nitric oxide to treat mammals generally requires that the gas be mixed with another gas, such as oxygen or oxygen-containing gas. This mixture requires very careful monitoring to be sure that the amount of nitric oxide in the gas administered to the mammal does not exceed predetermined limits. As used herein, the term "therapeutic gas" is intended to be limited to gases such as nitric oxide (NO) which are intended to treat a patient by modifying an underlying disorder in the physiology of the patient. Thus, as used herein, the term "therapeutic gas" is intended to exclude gases that do not have as their primary purpose the actual treatment of such an underlying disorder of the patient. Accordingly, gases such as anaesthesia are not included in the gas of interest here since the primary purpose of anaesthesia is not to treat an underlying disorder of the patient, but is only used as a tool to assist other means in treating a patient. Analgesics also fall into the category of gases excluded from the definition of therapeutic gas as used herein because analgesics are used for pain relief and thus treat only a symptom of a problem rather than the problem itself as is the case with the therapeutic gases such as NO and the like that are included in the definition of therapeutic gas as used herein.

Heretofore, such monitoring has been carried out using computers, or computer-based elements. Such elements are used to keep flow ratios between the nitric oxide and the mixing gas at preselected levels. However, such elements often are complicated and incorporate numerous calculations and measurements to determine the correct amount of gas to inject in order to provide a required concentration gas supply. Such systems thus have a time delay when a flow of one of the fluids changes. Often, such elements are not efficient in either high or low flow ranges or concentrations.

Still further, the complicated systems often result in loosely coupled, essentially open loop, control techniques that result in less accurate delivery over wide dynamic ranges of flow or rapid changes in flow due to the lack of feedback control.

Therefore, there is a need for a simple and accurate device and method to deliver NO or another therapeutic gas to a mammal.

There is still further need for a simple and accurate device and method to deliver NO or another therapeutic gas to a mammal through an external breathing circuit.

The need for accuracy requires a device and method for delivering such gases at a constant flow concentration regardless of inspiratory rates in order to be most effective in the treatment of diseases and injuries.

Some systems, such as the system disclosed in U.S. Pat. No. 4,932,401, use a system that set a ratio of one gas to another during the administration of gas to a patient. While this may be somewhat effective for the administration of an anaesthetic gas, such a control system may be difficult to accurately and rapidly control on the time scale of a single breath. Still further, the actual amount of one particular gas may be what is of interest and such amount may not be easily controlled if it can only be controlled as a part of a ratio. Such systems may be very inaccurate at very low rates of flow of one of the gases.

Still further, many presently-available systems must be very complicated in order to operate over a spectrum of flow ranges and concentrations. Such systems may become ungainly if all distorting factors are corrected for.

Therefore, there is a need for a device and method which has a wide dynamic range in order to deliver low concentrations into low flows and high concentrations into high flows.

There is a further need for a device and method which has a wide dynamic range in order to deliver low concentrations into low flows and high concentrations into high flows, yet is not complicated.

There is further need for a device and method which achieves accuracy associated with complicated computer-based systems yet without the attendant complications of such systems.

Some prior art systems, such as the system disclosed in U.S. Pat. No. 2,915,056, control the amount of anaesthesia gas applied to a patient according to the amount of that anaesthesia gas in the gas being exhaled by the patient. While this may be an effective means for controlling the administration of gases such as anaesthetic gases which are present in the gas exhaled by a patient, such means and methods will not be effective for the gas of interest to this disclosure which may be erratically and substantially absorbed by the patient, and thus may not be present in a deterministic ratio in the gas being exhaled by the patient. Thus, testing the exhaled gas for the presence of the administered gas will not work for systems that apply gases intended to treat the patient that are modified by the physiology of the patient.

Therefore, there is a need for a means and a method for accurately and efficiently controlling the administration of a gas that has as its primary purpose the treatment of a patient by modifying the underlying disorder in the physiology of the patient and which gas will be absorbed into the tissue of the patient.

OBJECTS OF THE INVENTION

It is a main object of the present invention to provide a simple and accurate device and method to deliver NO or another therapeutic gas to a mammal.

It is another object of the present invention to provide a means and a method for accurately and efficiently controlling the administration of a gas that has as its primary purpose the treatment of a patient by modifying an underlying disorder in the physiology of the patient and which will be absorbed into the tissue of the patient.

It is another object of the present invention to provide a simple and accurate device and method to deliver NO or another therapeutic gas to a mammal through an external breathing circuit.

It is another object of the present invention to provide a device and method for delivering such gases at a constant flow concentration regardless of inspiratory rates in order to be most effective in the treatment of diseases and injuries.

It is another object of the present invention to provide a device and method which has a wide dynamic range in order to deliver low concentrations into low flows and high concentrations into high flows.

SUMMARY OF THE INVENTION

These, and other, objects are achieved by a system for administering No to a mammal comprising a tube having an outlet end fluidically connected to a respiratory system of a mammal and conducting fluid to the respiratory system of the mammal and an inlet end; a total flow sensor having an No gas inlet, a breathing gas inlet, an outlet fluidically connected to the inlet end of said tube, a total flow of fluid out of the outlet of said total flow sensor being formed by a combination of NO gas flowing into the NO gas inlet and breathing gas flowing into the breathing gas inlet and flowing out of the outlet of said total flow sensor, a flow metering device positioned upstream of the outlet of said total flow sensor and downstream of the NO gas inlet and downstream of the breathing gas inlet, and a signal generator connected to the flow metering device of said total flow sensor and generating a signal corresponding to the total flow of fluid out of the outlet of said total flow sensor; a breathing gas source fluidically connected to the breathing gas inlet of said total flow sensor; an NO gas flow sensor fluidically connected to the NO gas inlet of said total flow sensor; a proportioning valve fluidically connected to said NO gas flow sensor; an NO gas source fluidically connected to said proportioning valve; a proportioning valve actuator connected to said proportioning valve and adjusting the amount of NO gas flowing through said proportioning valve; a closed loop flow control system connecting said total flow sensor and said proportioning valve actuator and controlling said proportioning valve actuator according to the total flow of fluid out of the outlet of said total flow sensor with the flow of NO gas being a fraction of the total flow of fluid out of the outlet of said total flow sensor.

The present invention is also embodied in a method of administering therapeutic gas to a mammal comprising providing a tube having an outlet end fluidically connected to a mammal and an inlet end; providing a source of breathing gas and generating a breathing gas flow from the source of breathing gas; providing a source of therapeutic gas and generating a therapeutic gas flow from the source of therapeutic gas; providing a total gas flow sensor; controlling the amount of therapeutic gas flowing to the total gas flow sensor to a regulated therapeutic gas flow; in the total gas flow sensor fluidically combining the breathing gas flow and the regulated therapeutic gas flow to define a total gas flow; conducting the majority of the gas flow to the mammal; generating a total gas flow signal corresponding to the total gas flow through the total gas flow sensor; attenuating the total gas flow signal to form an attenuated signal which corresponds to a signal corresponding to a fraction of the total gas flow through the total gas flow sensor; sensing the regulated therapeutic gas flow being combined with the breathing gas flow to form the total gas flow; generating a therapeutic gas flow signal corresponding to the flow of regulated therapeutic gas flow being combined with the breathing gas flow to form the total gas flow; combining the therapeutic gas flow signal with the attenuated signal to generate a control signal; and using the control signal to control the amount of therapeutic gas flowing to the total flow sensor from the source of therapeutic gas. It is here noted that the total flow of gas from the system embodying the present invention to a mammal may be different from the total flow of gas in the total gas flow sensor since some of the gas may be lost due to leaks, or tapped off for analysis or sampling, or the like.

The system and method of the present invention incorporates fast analog control techniques that eliminate many time delays associated with numerical calculations and measurements. The system and method provide for a more timely and precise adjustment of the flow control hardware and thus prevent the mis-dosing associated with slower acting systems and methods.

The system and method of the present invention have a wide dynamic range enabling the system to deliver low concentrations into low flows and high concentrations into high flows. This results from the analog control section using a closed loop feedback.

The use of gas injection upstream of the total flow measurement point allows the use of simple ratiometric feedback.

Injecting gas upstream of a bulk flow measurement flow region allows the feedback signal for the flow control hardware to be represented as a simple fraction of the delivered flow.

This provides for the mathematical representation of the flow control to be unconditionally stable for delivered concentrations that are substantially less than the source gas concentration.

The system and method of the present invention provides the ability to accurately inject gas into the flow measurement region to achieve a desired output gas concentration.

BRIEF DESCRIPTION OF THE DRAWING FIGURES

FIGS. 1A–1F are schematics showing various forms of the system embodying the teaching of the present invention.

FIG. 2 is a flow chart showing the method of the present invention.

DETAILED DESCRIPTION OF THE PREFERRED EMBODIMENT OF THE INVENTION

Other objects, features and advantages of the invention will become apparent from a consideration of the following detailed description and the accompanying drawings.

The system and method embodying the present invention use a closed loop feedback control system with simple ratiometric control to control the mixture of gas being applied to a patient. While NO is specifically discussed, it is understood that any therapeutic gas as the term is used herein can be substituted for the discussed NO without departing from the scope of the present disclosure. As is discussed in the incorporated documents, both breathing and application of the gas can be used.

Figure 1B:
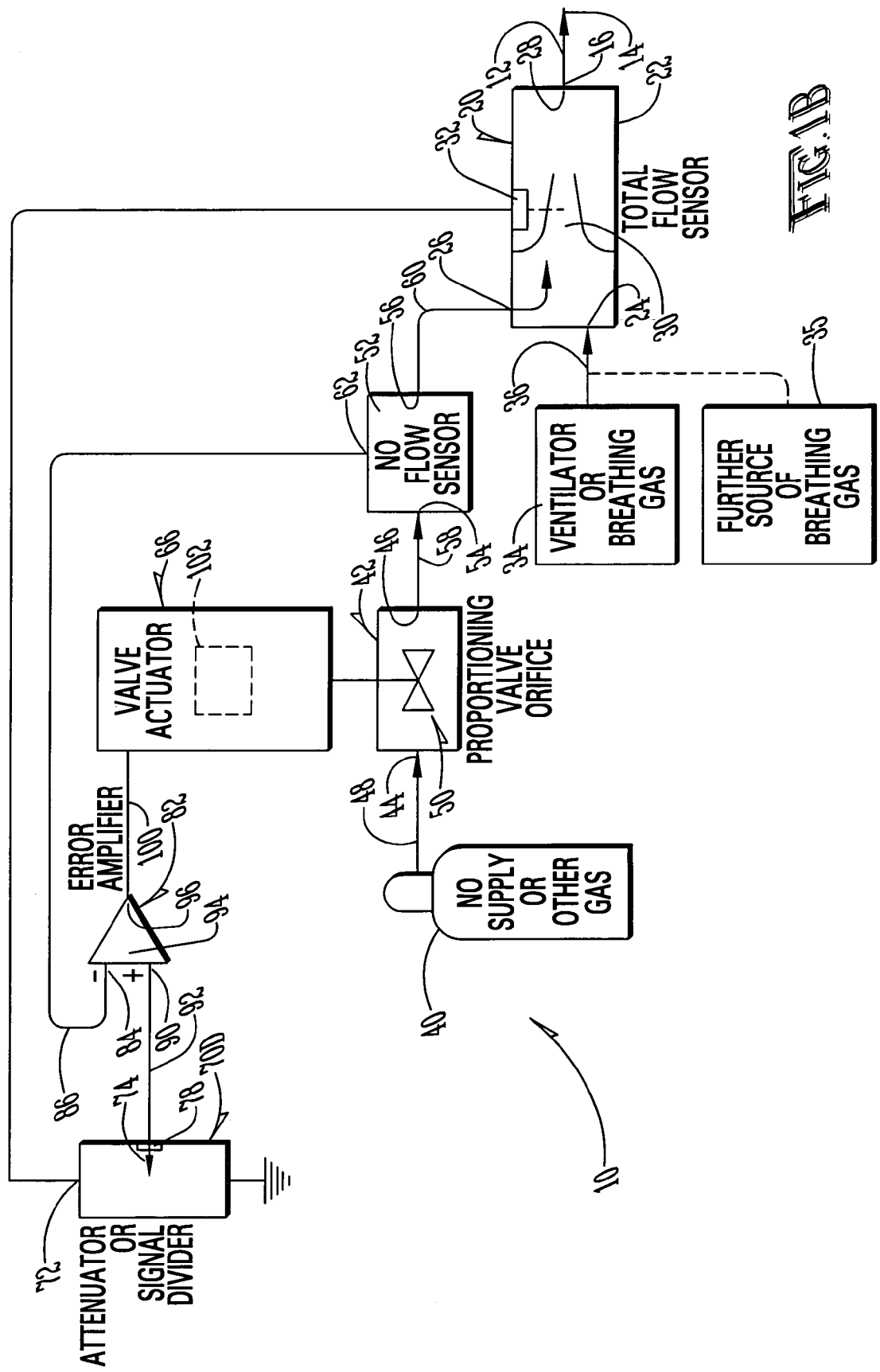
Figure 1F:
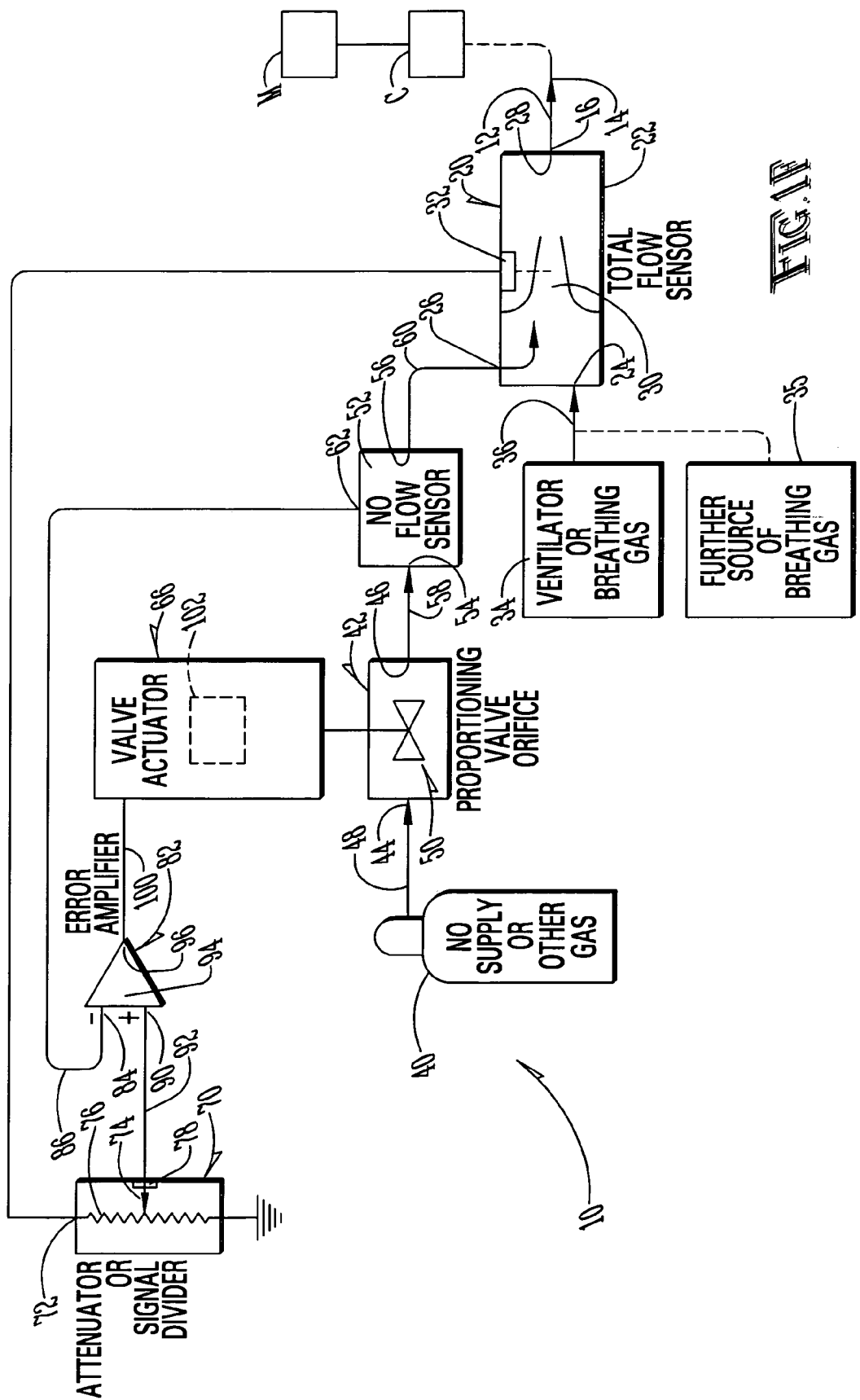

Referring to FIGS. 1A–1F, the present invention is embodied in a system 10 for administering NO to a mammal M comprising a tube 12 having an outlet end 14 fluidically connected to a respiratory system of a mammalian patient M and conducting fluid to the respiratory system of the mammalian patient, and an inlet end 16. As discussed in the incorporated material, the fluid can be applied to the patient by means of a mask K, a nasal cannula C or other such means as discussed in the incorporated documents. The pressure gradient used to draw fluid to the patient can be supplied by the patient or can be assisted by a ventilation assisting system, S.

System 10 further includes a total flow sensor 20 which includes a housing 22, a first fluid inlet 24 on housing 22, a second fluid inlet 26 on housing 22, a fluid outlet 28 on housing 22. Fluid outlet 28 is fluidically connected to inlet end 16 of tube 12 to transfer fluid thereto. Fluid flowing into housing 22 via first fluid inlet 24 combines in housing 22 of total flow sensor 20 with fluid flowing into housing 22 via second fluid inlet 26 of total flow sensor 20 to form a total fluid flow through housing 22. Total flow sensor 20 further includes a flow measuring device 30 in the housing, with measuring device 30 being positioned between the first and second inlets and the outlet of housing 22 to be located downstream of first fluid inlet 24 and downstream of second fluid inlet 26 and upstream of fluid outlet 28 and measuring the total fluid flow through housing 22. A signal generator 32 is connected to flow measuring device 30 in housing 22 of total flow sensor 20 and measures total flow of the flow from inlets 24 and 26 immediately downstream of where those two flows are mixed together. If there are any leaks in the flow circuit or other routes by which gas may be lost, the placement of signal generator 32 immediately downstream of the mixing point of the two gases automatically compensates for any fluid lost via a leak in the system. Thus, system 10 measures and controls exactly what ratio of therapeutic gas is being delivered to the patient, regardless of leaks of breathing gas upstream of the total flow sensor or leaks of mixed gas downstream of the total flow sensor. Signal generator 32 generates a signal corresponding to the total fluid flow through housing 22 of total flow sensor 20.

System 10 further includes a breathing gas supply 34. A fluid connection 36 fluidically connects breathing gas supply 34 to first inlet 24 on housing 22 of total flow sensor 20 and conducts gas from the breathing gas supply to the total flow sensor at a breathing gas flow rate. If desired and appropriate, a further source of breathing gas 35 can be fluidically connected to fluid connection 36 either directly as indicated in FIG. 1, or via control valves and sensors associated with the patient. The further source of breathing gas can be, like source 34, either oxygen, or oxygen-enriched air, room air, or even patient-generated air flow, or other such breathing gas as will be understood by those skilled in the art based on the teaching of this disclosure as well as the teaching of the disclosure in the incorporated material.

System 10 further includes a gas source 40 which is NO or other therapeutic gas. The following disclosure uses NO as the therapeutic gas; however, those skilled in the art will understand that other therapeutic gases as encompassed by the term as used herein, such as mentioned in the incorporated documents, such as carbon monoxide or others, can also be used without departing from the scope of the present invention. Accordingly, the disclosure of NO is for the sake of convenience and is not intended as a limitation. A proportioning orifice valve 42 has an inlet 44 and an outlet 46 and a fluid connection 48 fluidically connects NO gas source 40 to inlet 44 of proportioning orifice valve 42 and conducts NO gas to proportioning orifice valve 42. Proportioning orifice valve 42 includes a flow adjusting element 50 which is movable between a first configuration permitting full flow of NO from inlet 44 of proportioning orifice valve 42 to outlet 46 of proportioning orifice valve 42 and a second configuration preventing flow of NO from inlet 44 of proportioning orifice valve 42 to outlet 46 of proportioning orifice valve 42 and which can adopt any configuration therebetween as desired to adjust and control the flow of NO gas from NO gas supply 40 as will be understood from the teaching of this disclosure.

System 10 further includes an NO flow sensor 52 having an inlet 54 and an outlet 56. A fluid connection 58 fluidically connects outlet 46 of proportioning orifice valve 42 to inlet 54 of NO flow sensor 52 and conducts NO from outlet 46 of proportioning orifice valve 42 to inlet 54 of NO flow sensor 52. A fluid connection 60 fluidically connects outlet 56 of NO flow sensor 52 to second inlet 26 of housing 22 of total flow sensor 20. A signal generator 62 in NO flow sensor 52 generates a signal corresponding to the flow of NO from outlet 46 of proportioning orifice valve 42 to second inlet 26 of housing 22 of total flow sensor 20.

A valve actuator 66 is connected to flow adjusting element 50 of proportioning orifice valve 42 and controls movement of that flow adjusting element.

System 10 further includes a signal divider 70 having an electrical input signal connection 72 and an electrical output signal connection 74 and a signal proportioning element 76 electrically connecting input signal connection 72 of signal divider 70 to output signal connection 74 of signal divider 70 to adjust an output signal at output signal connection 74 to correspond to a signal corresponding to a fraction of the total fluid flow through housing 22 of total flow sensor 20. The fraction is equal to or greater than zero or less than or equal to unit. One form of signal divider is a variable resistor which can be set to adjust the fraction as desired by analog control 78, such as a knob, that can be manually set or set according to other means familiar to those skilled in the art of circuit design. Signal divider 70 can be adjusted to compensate the flow for various factors as determined by an operator whereby the amount of therapeutic gas applied to the patient as a fraction of total gas applied to the patient can account for variations desired by an operator by simply adjusting the signal divider as necessary. It is also noted that while signal divider 70 is shown as including an analog device, it can also include a digital device. A signal divider which includes a digital device is indicated as digital signal divider 70D in FIG. 1. Dotted and solid lines are used to indicate the alternative nature of the digital and analog forms of the signal divider.

An electrical connection 80 between signal generator 32 in total flow sensor 20 and input signal connection 72 of signal divider 70 transmits the signal corresponding to the total fluid flow through housing 22 of total flow sensor 20 is the input signal at input signal connection 72 of signal divider 70.

An error amplifier circuit 82 has a first signal input 84 electrically connected to signal generator 62 of NO flow sensor 52 by an electrical connector 86 to receive the signal generated by signal generator 62 of NO flow sensor 52 corresponding to the NO flowing from output 46 of NO proportioning orifice valve 42 to second inlet 26 of housing 22 of total flow sensor 20. Error amplifier circuit 82 further includes a second signal input 90 electrically connected by an electrical connector 92 to electrical output signal connection 74 of signal divider 70 to receive the output signal from signal divider 70. Error amplifier circuit 82 further includes a combining circuit 94 electrically connected to first signal input 84 of error amplifier circuit 82 and to second signal input 90 of error amplifier circuit and which combines signals received at the first and second signal inputs of error amplifier circuit 82 to form an output signal. An output signal generator 96 in error amplifier circuit 82 generates an output signal corresponding to the output signal of error amplifier circuit 82.

An electrical connection 100 between output signal generator 96 of error amplifier circuit 82 and valve actuator 66 conducts the output signal of error amplifier circuit 82 to valve actuator 66.

Valve actuator 66 has a circuit 102 which converts the output signal received from error amplifier circuit 82 to a positioning signal for flow adjusting element 50 of proportioning orifice valve 42.

Referring to FIG. 2, it can be understood that the present invention also comprises a method of administering therapeutic gas, such as NO to mammal M, such as a human or animal patient such as described in the incorporated material. The method comprises providing tube 12 having outlet end 14 fluidically connected to a mammal and an inlet end 16 in step 200; providing a source of breathing gas and generating a breathing gas flow from the source of breathing gas in step 202; providing a source of NO gas and generating an NO gas flow from the source of NO gas in step 204; providing a total gas flow sensor in step 206; controlling the amount of NO gas flowing to the total gas flow sensor to a regulated NO gas flow in step 208; in the total gas flow sensor fluidically combining the breathing gas flow and the regulated NO gas flow to define a total gas flow in step 210; conveying the majority of the gas flow to the mammal in step 212; generating a total gas flow signal corresponding to the total gas flow conducted from the outlet of the total gas flow sensor in step 214; attenuating the total gas flow signal to form an attenuated signal which corresponds to a signal corresponding to a fraction of the total gas flow from the total gas flow sensor in step 216; sensing the regulated NO gas flow being combined with the breathing gas flow to form the total gas flow in step 218; generating an NO gas flow signal corresponding to the flow of regulated NO gas flow being combined with the breathing gas flow to form the total gas flow in step 220; combining the NO gas flow signal with the attenuated signal to generate a control signal in step 222; and using the control signal to control the amount of NO gas flowing to the total flow sensor from the source of NO gas in step 224.

As mentioned above, an additional step, step 226, can be included in which the mammal provides a pressure gradient used to draw the therapeutic gas from the source of gas.

It is understood that while certain forms of the present invention have been illustrated and described herein, it is not to be limited to the specific forms or arrangements of parts described and shown.

What is claimed is:

1. A system for administering NO to a mammal through an external breathing circuit comprising:

A) a tube having an outlet end fluidically connected to a respiratory system of a mammalian patient and conducting fluid to the respiratory system of the mammalian patient, and an inlet end;

B) a total flow sensor which includes
  (1) a housing,
  (2) a first fluid inlet on the housing,
  (3) a second fluid inlet on the housing,
  (4) a fluid outlet on the housing and fluidically connected to the inlet end of said tube,
  (5) fluid flowing into the housing via the first fluid inlet combining in the housing of said total flow sensor with fluid flowing into the housing via the second fluid inlet of said total flow sensor to form a total fluid flow through said housing,
  (6) a flow measuring device in the housing, said flow measuring device being positioned between the first and second inlets and the outlet of the housing to be located downstream of the first fluid inlet and downstream of the second fluid inlet and upstream of the fluid outlet and measuring the total fluid flow through the housing, and
  (7) a signal generator connected to the flow measuring device in the housing of said total flow sensor and which generates a signal corresponding to the total fluid flow through the housing of said total flow sensor;

C) a breathing gas supply;

D) a fluid connection fluidically connecting said breathing gas supply to the first inlet on the housing of said total flow sensor;

E) breathing gas from said breathing gas supply being conducted to said total flow sensor at a breathing gas flow rate;

F) an NO gas source;

G) a proportioning orifice valve having an inlet and an outlet;

H) a fluid connection fluidically connecting said NO gas source to the inlet of said proportioning orifice valve and conducting NO gas to said proportioning orifice valve;

I) said proportioning orifice valve including a flow adjusting element which is movable between a first configuration permitting full flow of NO from the inlet of said proportioning orifice valve to the outlet of said proportioning orifice valve and a second configuration preventing flow of NO from the inlet of said proportioning orifice valve to the outlet of said proportioning orifice valve;

J) an NO flow sensor having an inlet and an outlet;

K) a fluid connection fluidically connecting the outlet of said proportioning orifice valve to the inlet of said NO flow sensor and conducting NO from the outlet of said proportioning orifice valve to the inlet of said NO flow sensor;

L) a fluid connection fluidically connecting the outlet of said NO flow sensor to the second inlet of the housing of said total flow sensor;

M) a signal generator in said NO flow sensor which generates a signal corresponding to the flow of NO from the outlet of said proportioning orifice valve to the second inlet of the housing of said total flow sensor;

N) a valve actuator connected to the flow adjusting element of said proportioning orifice valve;

O) a signal divider having an electrical input signal connection and an electrical output signal connection and a signal proportioning element electrically connecting the input signal connection of said signal divider to the output signal connection of said signal divider to adjust an output signal at the output signal connection to correspond to a signal corresponding to a fraction of the total fluid flow through the housing of said total flow sensor, the fraction being equal to or greater than zero and less than or equal to unity;

P) a control element on said signal divider;

Q) an electrical connection between the signal generator in said total flow sensor and the input signal connection of said signal divider whereby the signal corresponding to the total fluid flow through the housing of said total flow sensor is the input signal at the input signal connection of said signal divider;

R) an error amplifier circuit having
  (1) a first signal input electrically connected to the signal generator of said NO flow sensor to receive the signal generated by the signal generator of said NO flow sensor corresponding to the NO flowing from the output of said NO proportioning orifice valve to the second inlet of the housing of said total flow sensor,
  (2) a second signal input electrically connected to the electrical output signal connection of said signal divider to receive the output signal from said signal divider,
  (3) a combining circuit electrically connected to the first signal input of said error amplifier circuit and to the second signal input of said error amplifier circuit and which combines signals received at the first and second signal inputs of said error amplifier circuit to form an output signal, and
  (4) an output signal generator which generates an output signal corresponding to the output signal of said error amplifier circuit;

S) an electrical connection between the output signal generator of said error amplifier circuit and said valve actuator and which conducts the output signal of said error amplifier circuit to said valve actuator; and T) said valve actuator having a circuit which converts the output signal received from said error circuit amplifier circuit to a positioning signal for the flow adjusting element of said proportioning orifice valve.

2. The system defined in claim 1 wherein the proportioning element of said signal divider includes a variable resistor.

3. The system defined in claim 1 wherein said breathing gas is oxygen.

4. The system defined in claim 1 wherein said breathing gas is oxygen-enriched air.

5. The system defined in claim 1 further including a further source of breathing gas.

6. The system defined in claim 5 further including a ventilation device fluidically connecting said further source of breathing gas to the mammal.

7. The system defined in claim 1 further including a nasal cannula fluidically connected to the outlet end of said tube.

8. The system defined in claim 1 further including a mask fluidically connected to the outlet end of said tube.

9. The system defined in claim 1 said signal divider includes an analog element.

10. The system defined in claim 1 wherein said signal divider includes a digital element.

11. A system for administering NO to a mammal comprising:

A) a tube having an outlet end fluidically connected to a respiratory system of a mammal and conducting fluid to the respiratory system of the mammal and an inlet end;

B) a total flow sensor having
  (1) an NO gas inlet,
  (2) a breathing gas inlet,
  (3) an outlet fluidically connected to the inlet end of said tube,
  (4) a total flow of fluid out of the outlet of said total flow sensor being formed by a combination of NO gas flowing into the NO gas inlet and breathing gas flowing into the breathing gas inlet and flowing out of the outlet of said total flow sensor,
  (5) a flow measuring device positioned upstream of the outlet of said total flow sensor and downstream of the NO gas inlet and downstream of the breathing gas inlet, and
  (6) a signal generator connected to the flow measuring device of said total flow sensor and generating a signal corresponding to the total flow of fluid out of the outlet of said total flow sensor;

C) a breathing gas source fluidically connected to the breathing gas inlet of said total flow sensor;

D) an NO gas flow sensor fluidically connected to the NO gas inlet of said total flow sensor;

E) a proportioning valve fluidically connected to said NO gas flow sensor;

F) an NO gas source fluidically connected to said proportioning valve;

G) a proportioning valve actuator connected to said proportioning valve and adjusting the amount of NO gas flowing through said proportioning valve;

H) a closed loop flow control system connecting said total flow sensor and said proportioning valve actuator and controlling said proportioning valve actuator according to the total flow of fluid out of the outlet of said total flow sensor with the flow of NO gas being a fraction of the total flow of fluid out of the outlet of said total flow sensor.

12. The system defined in claim 11 wherein said closed loop flow control system includes a signal divider electrically connected to said total flow sensor and generating an output signal which corresponds to a fraction of the total flow of fluid out of the outlet of said total flow sensor.

13. The system defined in claim 12 wherein said signal divider includes a variable resistor.

14. The system defined in claim 11 wherein said closed loop flow control system further includes an amplifier electrically connected to the NO gas flow sensor and to said signal divider and to said proportioning valve actuator.

15. A system for administering therapeutic gas to a mammal through an external breathing circuit comprising:

A) a tube having an outlet end fluidically connected to a respiratory system of a mammalian patient and conducting fluid to the respiratory system of the mammalian patient, and an inlet end;

B) a total flow sensor which includes
  (1) a housing,
  (2) a first fluid inlet on the housing,
  (3) a second fluid inlet on the housing,
  (4) a fluid outlet on the housing and fluidically connected to the inlet end of said tube,
  (5) fluid flowing into the housing via the first fluid inlet combining in the housing of said total flow sensor with fluid flowing into the housing via the second fluid inlet of said total flow sensor to form a total fluid flow through said housing,
  (6) a flow metering device in the housing, said flow measuring device being positioned between the first and second inlets and the outlet of the housing to be located downstream of the first fluid inlet and downstream of the second fluid inlet and upstream of the fluid outlet and measuring the total fluid flow through the housing, and
  (7) a signal generator connected to the flow measuring device in the housing of said total flow sensor and which generates a signal corresponding to the total fluid flow through the housing of said total flow sensor;

C) a breathing gas supply;

D) a fluid connection fluidically connecting said breathing gas supply to the first inlet on the housing of said total flow sensor;

E) breathing gas from said breathing gas supply being conducted to said total flow sensor at a breathing gas flow rate;

F) a therapeutic gas source;

G) a proportioning orifice valve having an inlet and an outlet;

H) a fluid connection fluidically connecting said therapeutic gas source to the inlet of said proportioning orifice valve and conducting therapeutic gas to said proportioning orifice valve;

I) said proportioning orifice valve including a flow adjusting element which is movable between a first configuration permitting full flow of therapeutic gas from the inlet of said proportioning orifice valve to the outlet of said proportioning orifice valve and a second configuration preventing flow of therapeutic gas from the inlet of said proportioning orifice valve to the outlet of said proportioning orifice valve;

J) an therapeutic gas flow sensor having an inlet and an outlet;

K) a fluid connection fluidically connecting the outlet of said proportioning orifice valve to the inlet of said therapeutic gas flow sensor and conducting therapeutic gas from the outlet of said proportioning orifice valve to the inlet of said therapeutic gas flow sensor;

L) a fluid connection fluidically connecting the outlet of said therapeutic gas flow sensor to the second inlet of the housing of said total flow sensor;

M) a signal generator in said therapeutic gas flow sensor which generates a signal corresponding to the flow of therapeutic gas from the outlet of said proportioning orifice valve to the second inlet of the housing of said total flow sensor;

N) a valve actuator connected to the flow adjusting element of said proportioning orifice valve;

O) a signal divider having an electrical input signal connection and an electrical output signal connection and a signal proportioning element electrically connecting the input signal connection of said signal divider to the output signal connection of said signal divider to adjust an output signal at the output signal connection to correspond to a signal corresponding to a fraction of the total flow through said total flow sensor, the fraction being equal to or greater than zero and less than or equal to unity;

P) an analog control element on said signal divider;

Q) an electrical connection between the signal generator in said total flow sensor and the input signal connection of said signal divider whereby the signal corresponding to the total fluid flow through the housing of said total flow sensor is the input signal at the input signal connection of said signal divider;

R) an error amplifier circuit having
  (1) a first signal input electrically connected to the signal generator of said therapeutic gas flow sensor to receive the signal generated by the signal generator of said therapeutic gas flow sensor corresponding to the therapeutic gas flowing from the outlet of said therapeutic gas proportioning orifice valve to the second inlet of the housing of said total flow sensor,
  (2) a second signal input electrically connected to the electrical output signal connection of said signal divider to receive the output signal from said signal divider,
  (3) a combining circuit electrically connected to the first signal input of said error amplifier and to the second signal input of said error amplifier and which combines signals received at the first and second signal inputs of said error amplifier circuit to form an output signal, and
  (4) an output signal generator which generates an output signal corresponding to the output signal of said error amplifier circuit;

S) an electrical connection between the output signal generator of said error amplifier circuit and said valve actuator and which conducts the output signal of said error amplifier circuit to said valve actuator; and T) said valve actuator having a circuit which converts the output signal received from said error circuit amplifier circuit to a positioning signal for the flow adjusting element of said proportioning orifice valve.

16. A system for administering therapeutic gas to a mammal comprising:

A) a tube having an outlet end fluidically connected to a respiratory system of a mammal and conducting fluid to the respiratory system of the mammal and an inlet end;

B) a total flow sensor having
  (1) a therapeutic gas inlet,
  (2) a breathing gas inlet,
  (3) an outlet fluidically connected to the inlet end of said tube,
  (4) a total flow of fluid out of the outlet of said total flow sensor being formed by a combination of therapeutic gas flowing into the therapeutic gas inlet and breathing gas flowing into the breathing gas inlet and flowing out of the outlet of said total flow sensor,
  (5) a flow measuring device positioned upstream of the outlet of said total flow sensor and downstream of the therapeutic gas inlet and downstream of the breathing gas inlet, and
  (6) a signal generator connected to the flow measuring device of said total flow sensor and generating a signal corresponding to the total flow of fluid out of the outlet of said total flow sensor;

C) a breathing gas source fluidically connected to the breathing gas inlet of said total flow sensor;

D) an therapeutic gas flow sensor fluidically connected to the therapeutic gas inlet of said total flow sensor;

E) a proportioning valve fluidically connected to said therapeutic gas flow sensor;

F) an therapeutic gas source fluidically connected to said proportioning valve;

G) a proportioning valve actuator connected to said proportioning valve and adjusting the amount of therapeutic gas flowing through said proportioning valve;

H) a closed loop flow control system connecting said total flow sensor and said proportioning valve actuator and controlling said proportioning valve actuator according to the total flow of fluid out of the outlet of said total flow sensor with the flow of therapeutic gas being a fraction of the total flow of fluid out of the outlet of said total flow sensor.

17. A system for administering gas which treats a physiological problem of a mammal comprising:

A) a source of treatment gas of the type used to treat physiological problems of mammals;

B) a source of treatment gas of the type used by mammals to breath;

C) a total flow sensor having
  (1) a treatment gas inlet,
  (2) a breathing gas inlet, (3) an outlet fluidically connected to a mammal being treated, (4) a total flow out of the outlet of said total flow sensor comprised of treatment gas flowing into said total flow sensor via the treatment gas inlet and breathing gas flowing into said total flow sensor via said breathing gas inlet, and (5) a signal generator fluidically connected to the total flow out of the outlet of said total flow sensor and which generates signals corresponding to the total flow out of the outlet of said total flow sensor;

D) a control valve fluidically connected to said source of treatment gas and controlling the amount of treatment gas flowing out of said source of treatment gas and into the treatment gas inlet of said total flow sensor;

E) a valve actuator connected to said control valve and controlling operation of said control valve; and F) a signal attenuator connected to said valve actuator and to said total flow sensor, said signal attenuator receiving the signal generated by the signal generator of said total flow sensor corresponding to the total flow out of the outlet of said total flow sensor and attenuating the signal corresponding to the total flow out of the outlet of said total flow sensor and generating an attenuated signal that corresponds to a fraction of the total flow out of the outlet of said total flow sensor, the attenuated signal generated by said signal attenuator being received by said valve actuator to set said valve actuator to a position which controls flow from said source of treatment gas to a flow that corresponds to the fraction of the total flow out of the outlet of said total flow sensor whereby flow of treatment gas from said source of treatment gas corresponds to a fraction of the total flow out of the outlet of said total flow sensor.

18. A method of administering NO to a mammal comprising:

A) providing a tube having an outlet end fluidically connected to a mammal and an inlet end;

B) providing a source of breathing gas and generating a breathing gas flow from the source of breathing gas;

C) providing a source of NO gas and generating an NO gas flow from the source of NO gas;

D) providing a total gas flow sensor;

E) controlling the amount of NO gas flowing to the total gas flow sensor to a regulated NO gas flow;

F) in the total gas flow sensor fluidically combining the breathing gas flow and the regulated NO gas flow to define a total gas flow;

G) conveying the total gas flow to the mammal;

H) generating a total gas flow signal corresponding to the total gas flow conducted to the mammal;

I) attenuating the total gas flow signal to form an attenuated signal which corresponds to a signal corresponding to a fraction of the total gas flow to the mammal;

J) sensing the regulated NO gas flow being combined with the breathing gas flow to form the total gas flow;

K) generating an NO gas flow signal corresponding to the flow of regulated NO gas flow being combined with the breathing gas flow to form the total gas flow;

L) combining the NO gas flow signal with the attenuated signal to generate a control signal; and M) using the control signal to control the amount of NO gas flowing to the total flow sensor from the source of NO gas.

19. The method defined in claim 18 further including a step of the mammal providing a pressure gradient used to draw the total gas flow from the total gas flow sensor.

20. A method of administering therapeutic gas to a mammal comprising:

A) providing a tube having an outlet end fluidically connected to a mammal and an inlet end;

B) providing a source of breathing gas and generating a breathing gas flow from the source of breathing gas;

C) providing a source of therapeutic gas and generating an therapeutic gas flow from the source of therapeutic gas;

D) providing a total gas flow sensor;

E) controlling the amount of therapeutic gas flowing to the total gas flow sensor to a regulated therapeutic gas flow;

F) in the total gas flow sensor fluidically combining the breathing gas flow and the regulated therapeutic gas flow to define a total gas flow;

G) conveying the total gas flow to the mammal;

H) generating a total gas flow signal corresponding to the total gas flow conducted to the mammal;

I) attenuating the total gas flow signal to form an attenuated signal which corresponds to a signal corresponding to a fraction of the total gas flow to the mammal;

J) sensing the regulated therapeutic gas flow being combined with the breathing gas flow to form the total gas flow;

K) generating an therapeutic gas flow signal corresponding to the flow of regulated therapeutic gas flow being combined with the breathing gas flow to form the total gas flow;

L) combining the therapeutic gas flow signal with the attenuated signal to generate a control signal; and M) using the control signal to control the amount of therapeutic gas flowing to the total flow sensor from the source of therapeutic gas.

* * * * *